US009193690B2

(12) United States Patent
Gil

(10) Patent No.: US 9,193,690 B2
(45) Date of Patent: *Nov. 24, 2015

(54) PHARMACEUTICAL COMPOSITIONS COMPRISING (3-(1-(1H-IMIDAZOL-4-YL)ETHYL)-2-METHYLPHENYL)METHANOL

(71) Applicant: Allergan, Inc., Irvine, CA (US)

(72) Inventor: Daniel W. Gil, Corona del Mar, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/550,647

(22) Filed: Nov. 21, 2014

(65) Prior Publication Data

US 2015/0080445 A1    Mar. 19, 2015

Related U.S. Application Data

(63) Continuation of application No. 13/147,760, filed as application No. PCT/US2010/024111 on Feb. 12, 2010, now abandoned.

(60) Provisional application No. 61/152,494, filed on Feb. 13, 2009.

(51) Int. Cl.
*C07D 233/64* (2006.01)
*A61K 31/4174* (2006.01)

(52) U.S. Cl.
CPC .......... *C07D 233/64* (2013.01); *A61K 31/4174* (2013.01)

(58) Field of Classification Search
CPC ........................ A61K 31/4174; C07D 233/64
See application file for complete search history.

(56) References Cited

U.S. PATENT DOCUMENTS

| | | | |
|---|---|---|---|
| 4,166,452 A | 9/1979 | Generales et al. | |
| 4,256,108 A | 3/1981 | Theeuwes | |
| 4,265,874 A | 5/1981 | Bonsen et al. | |
| 5,091,402 A | 2/1992 | Kalso et al. | |
| 5,344,840 A | 9/1994 | Maze et al. | |
| 7,098,200 B2 | 8/2006 | Brandt et al. | |
| 8,492,422 B2 * | 7/2013 | Dibas et al. | 514/400 |
| 8,492,557 B2 * | 7/2013 | Chow et al. | 548/346.1 |
| 8,501,796 B2 * | 8/2013 | Dibas et al. | 514/396 |
| 8,653,123 B2 * | 2/2014 | Dibas et al. | 514/396 |
| 8,853,251 B2 * | 10/2014 | Dibas et al. | 514/396 |

FOREIGN PATENT DOCUMENTS

| | | |
|---|---|---|
| EP | 0331374 A2 | 9/1989 |
| EP | 0424059 A1 | 4/1991 |

OTHER PUBLICATIONS

Stoilov et al., "Synthesis of Detomidine and Medetomidine Metabolites: 1,2,3-Trisbustituted Arenes with 4'(5')-Imidazoylmethyl Groups." J. Heterocyclic Chem., 20, pp. 1645-1651 (1993).*
Beeley, Lee et al, Synthesis of a Selective Alpha-2A Adrenoceptor Antagonist, BRL 48962, and Its Characterization at Cloned Human Alpha-Adrenoceptors, Bioorganic & Medicinal Chemistry, 1995, 1693-1698, 3(12).
Conklin, et al., Substitution of three amino acids switches receptor specificity of Gqa to that of Gia, Letters of Nature, May 20, 1993, 274-246, 363, US.
Gil, DW et al, Transient Allodynia Pain Models in Mice for Early Assessment of Analgesic Activity, British Journal of Pharmacology, 2008, 769-774, 153.
Hui, Y. H. et al, Analytical Method Development for the Simultaneous Quantitation of Dexmedetomidine and Three Potential Metabolites in Plasma, Journal of Chromatography, 1997, 281-291, 762, US.
Hunter, J.C. et al, Assessment of the Role of α2-Adrenoceptor Subtypes in the Antinociceptive, Sedative and Hypothermic Action of Dexmedetomidine in Transgenic Mice, British Journal of Pharmacology, 1997, 1339-1344, 122.
Kavanagh, Pierce et al, Synthesis of Possible Metabolites of Medetomidine {1-(2,3-Dimethylphenyl)-1-[imidazol-4(5)-yl]ethane}, J. Chem. Research, 1993, 152-153, 4.
Lavand'Homme, Patricia et al, Peripheral Nerve Block with Clonidine Produces Antiallodynic Effect Mediated by Alpha2A-Adrenergic Receptor at Nerve Injury Site in Neuropathic Rats, Asa Abstracts, 2001, A975, 95.
Millan, Mark et al, Evidence that an α2A-adrenoceptor Subtype Mediates Antinociception in Mice, European Journal of Pharmacology, 1992, 355-356, 215.
Minami, Toshiaki et al, Allodynia Evoked by Intrathecal Administration of Prostaglandin E2 to Conscious Mice, Pain, 1994, 217-223, 57.
Remington's Pharmaceutical Sciences, 16th Edition, 10 Pages, 1980.
Salonen, Jarmo, Biotransformation of Medetomidine in the Rat, Xenobiotica, 1990, 471-480, 20(5).
Patent Cooperation Treaty, Notification of Transmittal of the International Search Report and the Written Opinion of the International Searching Authority, or the Declaration, Form PCT/ISA/220, Int. App. No. PCT/US2010/024111, Apr. 27, 2010.

* cited by examiner

*Primary Examiner* — Sreeni Padmanabhan
*Assistant Examiner* — Jody Karol
(74) *Attorney, Agent, or Firm* — Barbara C. Potts

(57) ABSTRACT

Disclosed herein is a pharmaceutical composition comprising (3-(1-(1H-imidazol-4-yl)ethyl)-2-methylphenyl)methanol and methods of using the composition to treat chronic pain.

12 Claims, No Drawings

PHARMACEUTICAL COMPOSITIONS COMPRISING (3-(1-(1H-IMIDAZOL-4-YL)ETHYL)-2-METHYLPHENYL)METHANOL

CROSS REFERENCE

This application is a continuation of, and claims priority to, U.S. patent application Ser. No. 13/147,760, filed Aug. 25, 2011, which is a national stage application filed under 35 U.S.C. §371 of International Application No. PCT/US10/24111, filed on Feb. 12, 2010, which claims priority to and the benefit of U.S. Provisional Patent Application No. 61/152,494 filed on Feb. 13, 2009, the disclosure of each of which is hereby incorporated by reference in its entirety.

Disclosed herein are compounds having the structure

Compound I

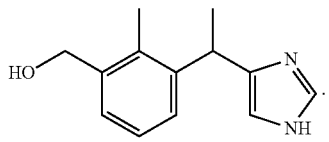

The structure depicted above includes the following tautomeric forms:

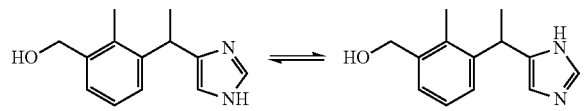 [SMILES: Cc1c(CO)cccc1C(C)c1c[nH]cn1 ; Cc1c(CO)cccc1C(C)c1cnc[nH]1]

Compound I is (3-(1-(1H-imidazol-4-yl)ethyl)-2-methylphenyl)methanol. It occurs as two enantiomers:

Compound II

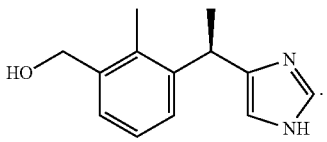

Compound III

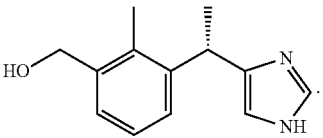

Compound II is (R)-(3-(1-(1H-imidazol-4-yl)ethyl)-2-methylphenyl)methanol;
Compound III is (S)-(3-(1-(1H-imidazol-4-yl)ethyl)-2-methylphenyl)methanol. These compounds are formed by the in vivo hydroxylation of medetomidine (5-(1-(2,3-dimethylphenyl)ethyl)-1H-imidazole):

Compound IV

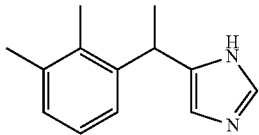

Medetomidine is well known in the art. The hydrochloride salt of the (S) enantiomer of medetomidine is sold in the United States under the brand name Precedex® for the sedation of initially intubated and mechanically ventilated patients during treatment in an intensive care setting. The racemic mixture (medetomidine) is sold in the United States for use in the sedation of animals.

Metabolites of medetomidine and dexmedetomidine are known, and are described in I. Stoilov, et al., Synthesis of detomidine and medetomidine metabolites: 1,2,3-trisubstituted arenes with 4'(5')-imidazolylmethyl groups, *J. Heterocyclic Chem.* 30:6, 1645-51 (1993); P. V. Kavanagh et al., Synthesis of possible metabolites of medetomidine {1-(2,3-dimethylphenyl)-1-[imidazol-4(5)-yl]ethane}, *J. Chem. Res. Synopses* 4, 152-3 (1993); J. S. Salonen and M. Eloranta, Biotransformation of medetomidine in the rat, *Xenobiotica* 20:5, 471-80 (1990); Y-H Hui et al., Analytical method development for the simultaneous quantitation of dexmedetomidine and three potential metabolites in plasma, *J. Chromatog.*, 762, 281-291 (1997).

The inventors have discovered that, whereas medetomidine is sedating—indeed, whereas the compounds is marketed for its sedative properties—the compounds of the invention may be used to treat chronic pain without sedation.

Synthesis

Compounds of Formula I may be synthesized as follows.

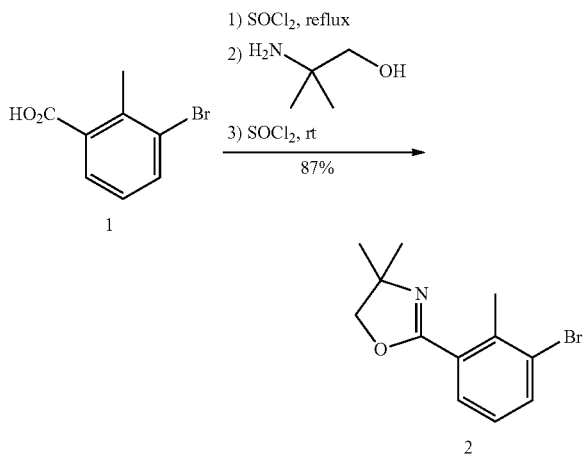

Procedure:

To a 1 L, one-necked flask equipped with a magnetic stir bar and reflux condenser, was added 3-bromo-2-methylbenzoic acid 1 (200 g, 0.93 mol) and thionyl chloride (202 mL, 2.79 mol). The reactor was attached to aqueous NaOH solution scrubber (the amount of NaOH was not listed above) and heated to 76° C. for 90 min. At this point, all the solid had dissolved. GC analysis indicated that the reaction was complete. The batch was cooled to ambient temperature and concentrated under reduced pressure to give 3-bromo-2-methylbenzoyl chloride as a light brown oil. This material was dissolved in anhydrous $CH_2Cl_2$ (350 mL) and transferred to an addition funnel. This solution was added drop wise to a solution of 2-amino-2-methyl-1-propanol (182.4 g, 2.05 mol) in anhydrous $CH_2Cl_2$ (1.0 L) over 45 min. During the addition, the internal temperature was kept between 10° C. to 20° C. by cooling with an ice-water bath. The addition funnel was rinsed with anhydrous $CH_2Cl_2$ (50 mL). The batch was stirred at ambient temperature for 3 h. GC analysis indicated that the reaction was complete. The salts were filtered-off and the filter cake was rinsed with $CH_2Cl_2$ (1 L). The filtrate was washed with sat. aq $NaHCO_3$ (500 mL, prepared from 200 g NaHCO₃ and 1.6 L tap water) and brine (500 mL, prepared from 750 g NaCl and 1.5 L tap water). The separated organic layer was dried over Na₂SO₄ (400 g) and filtered. Material transfer and filter cake rinsing was completed with CH₂Cl₂ (1 L). The filtrate was concentrated under reduced pressure. To the resulting residue was slowly added thionyl chloride (302 mL, 4.16 mol). Exothermic reaction occurred. The reactor was attached to aqueous NaOH solution scrubber (the amount of NaOH was not listed above) and the batch was stirred for 2 h upon completion of the addition. GC analysis indicated that the reaction was complete. Thionyl chloride was removed under reduced pressure. The residue was cooled with an ice-water bath. MeOH (100 mL) was slowly added (very exothermic), followed by 20 wt % NaOH solution (600 mL, prepared from 200 g NaOH and 0.8 L tap water). The pH of the reaction mixture was determined to be 14. Tap water (1 L) was added, and the batch was stirred until most of the solids dissolved. The mixture was extracted with MTBE (800 mL×3). The organic layers were combined, washed with brine (500 mL), dried over Na₂SO₄ (322 g), and concentrated under reduced pressure. The residue was purified by passage through a silica-gel plug (1 kg silica gel in a 3 L filter funnel loaded with 2 L of hexane) eluted with 15% EtOAc/hexane (7.5 L). The first 5.5 L of eluent contained 2. Concentration under reduced pressure afforded 217 g (87%) of 2 as an orange oil. HPLC indicated its purity was 96.5 A %. LCMS (m/z) 268.14 (M⁺+1, ⁷⁹Br), 270.03 (M⁺+1, ⁸¹Br). ¹H NMR (400 MHz, CDCl₃) δ 1.40 (6H, s), 2.61 (3H, s), 4.09 (2H, s), 7.06 (1H, dd, J=8.4, 7.2 Hz), 7.60 (1H, d, J=7.2 Hz), 7.62 (1H, dd, J=8.4, 1.2 Hz). ¹³C NMR (100 MHz, CDCl₃) δ 20.9, 28.5 (2C), 68.2, 79.0, 126.7, 126.8, 129.0, 130.3, 134.7, 137.9, 162.3.

once; the mixture was refluxed overnight. After cooled to ambient temperature, the mixture was cooled with ice-water bath. Saturated aq NH₄Cl (500 mL, prepared from 600 g of NH₄Cl and 1.65 L of tap water) was added, keeping the internal temperature below 24° C. After addition was completed, cooling was removed and the mixture was stirred at ambient temperature for 40 min. The layers were separated; the organic layer was washed with saturated aq NH₄Cl (250 mL), dried over anhydrous MgSO₄ (10 g), filtered, and concentrated under reduced pressure. The resulting oily solid (75.1 g) was swished with 10% EtOAc-hexane (300 mL) for 1 h. The retained aqueous layer was extracted with EtOAc (500 mL), and the organic layer dried over MgSO₄ (5 g), filtered, and concentrated under reduced pressure. Residual solids from the second extract (3.3 g) were swished with 10% EtOAc-hexane (100 mL) for 1 h. Both batches of swished material were filtered and combined, then rinsed with 10% EtOAc-hexane (100 mL). The combined solid was dried under high vacuum to give 19.1 g (72% based on 4(5)-imidazolecarboxaldehyde) of an off-white powder. HPLC analysis indicated it to be a ~4:1 mixture of 3 and 4. LCMS (m/z) 286.14 (M⁺+1). ¹H NMR (400 MHz, CD₃OD) δ 1.38 (6H, s), 2.33 (3H, s), 4.17 (2H, s), 6.05 (1H, s), 6.65 (1H, s), 7.30 (1H, t, J=7.6 Hz), 7.46 (1H, dd, J=8.0, 1.2 Hz), 7.63 (1H, s), 7.73 (1H, d, J=7.6 Hz). ¹³C NMR (100 MHz, CD₃OD) δ 16.2, 28.6 (2C), 67.8, 68.7, 80.5, 118.7, 126.8, 129.7, 130.0, 130.2, 136.1, 136.8, 141.4, 144.0, 166.6.

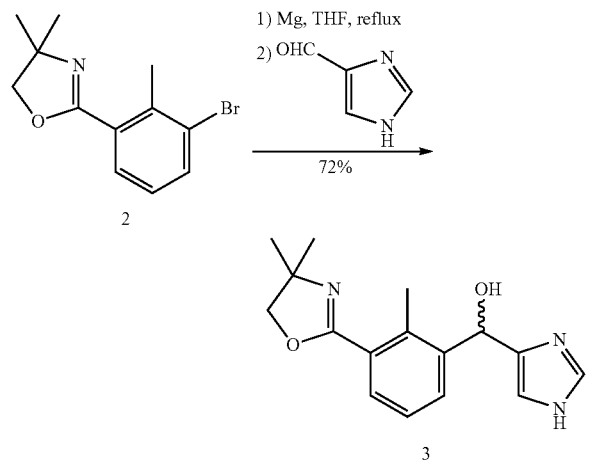

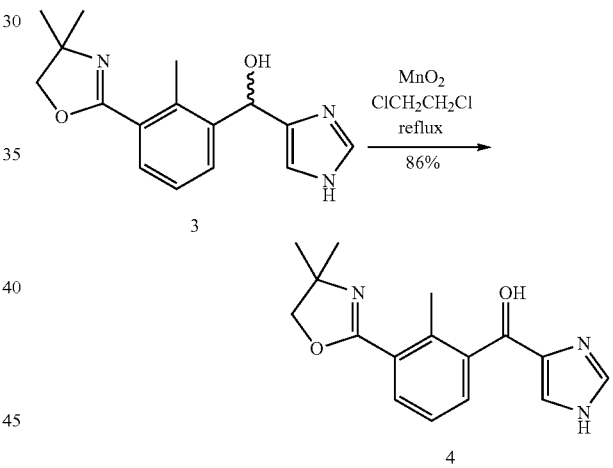

Procedure:

A 5 L, three-necked flask was equipped with a stir bar, a reflux condenser with N₂ inlet, a thermocouple, and a stopper. To it was charged 3 (81.0 g, 0.28 mol, ~4:1 mix with 4), MnO₂ (243.4 g, 2.80 mol), and 1,2-dichloroethane (2.6 L). The mixture was stirred at 75° C. for 1 h. At this point, HPLC analysis indicated that the reaction was complete. Heating was halted and the mixture cooled to 60° C. The batch was filtered through a Celite pad (500 g, packed with 1 L of 1,2-dichloroethane), and the filter cake rinsed with THF (6 L). The filtrate and wash were concentrated to a small volume (~350 mL), and hexane (3 L) was added in a thin stream with stirring. After stirring for 15 min the solids were collected, the filter cake was rinsed with hexane (200 mL), then it was dried under reduced pressure at 60° C. for 6 h. Thus was obtained 68.0 g (86%) of 4 as a powder. ¹H NMR analysis indicated it the presence of ~5 mol % THF. LCMS (m/z) 284.26 (M⁺+1). ¹H NMR (400 MHz, CD₃OD) δ 1.39 (6H, s), 2.41 (3H, s), 4.20 (2H, s), 7.37 (1H, t, J=7.6 Hz), 7.48 (1H, s), 7.53 (1H, d, Procedure:

A 3 L, four-necked flask was equipped with a magnetic stir bar, a thermocouple, an addition funnel, and a reflux condenser with N₂ inlet. To it were charged with Mg turnings (4.76 g, 0.196 mol) and anhydrous THF (20 mL). Next, 1,2-dibromoethane (0.5 mL) was added and vigorous stirring was performed for a few minutes. Activation of the Mg became evident (bubbling, blackening). The batch was heated to 55° C., and a solution of 2 (50 g, 0.186 mol) in anhydrous THF (480 mL) was added over 10 min. An exothermic reaction started and it persisted for 10 min. Most of the Mg had dissolved at this point and the mixture had turned to a greenish suspension. Heating at reflux was continued for 30 min. A solution of 4(5)-imidazolecarboxaldehyde (8.94 g, 0.093 mol) dissolved in anhydrous THF (250 mL) was added all at J=7.6 Hz), 7.72 (1H, d, J=7.6 Hz), 7.93 (1H, s). $^{13}$C NMR (100 MHz, CD$_3$OD) δ 17.8, 28.6 (2C), 68.9, 80.6, 126.7, 130.9, 131.2, 132.5 (2C), 136.9, 138.6, 140.6, 142.0, 165.6, 190.5.

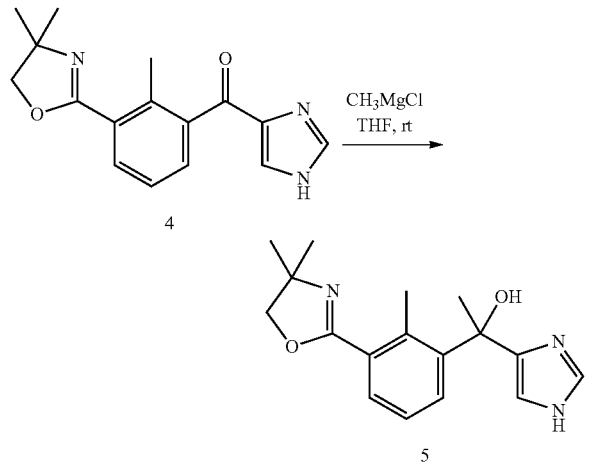

Procedure:

A three-necked, 5 L flask equipped with a magnetic stir bar, reflux condenser, N$_2$ inlet, and addition funnel was charged with 4 (139.0 g, 0.49 mol) and THF (3.2 L). To the stirred solution was added MeMgCl (22 wt % in THF, 542.0 g), keeping the internal temperature below 40° C. When addition was complete, the batch was heated at 65° C. for 3 h and eventually became dark brown. At this point, TLC analysis showed the reaction to be complete. The batch was cooled with ice-water bath to 10° C. The reaction was quenched by drop wise addition of saturated aq NH$_4$Cl (1.0 L, prepared from 835 g of NH$_4$Cl and 2.5 L of tap water) to the mixture while keeping the internal temperature below 20° C. After this addition was complete, the layers were separated. The organic layer was washed with a 1:2 mixture of tap water (500 mL) and brine (1000 mL, prepared from 1 kg of NaCl and 2 L of tap water), and the layers were separated. The organic layer was washed with brine (300 mL, as above), separated, and dried over MgSO$_4$ (100 g). After filtration, it was concentrated under reduced pressure. The residue was dried under the high vacuum to give 162.8 g of 5 as a brown foam. $^1$H NMR analysis indicated that the material contaminated some EtOAc and THF but was pure enough to carry on to the next step without further purification. LCMS (m/z) 300.22 (M$^+$+ 1). $^1$H NMR (400 MHz, CD$_3$OD) δ 1.36 (6H, s), 1.92 (3H, s), 2.16 (3H, s), 4.15 (2H, s), 6.82 (1H, s), 7.26 (1H, dd, J=8.0, 7.2 Hz), 7.38 (1H, d, J=7.2 Hz), 7.57 (1H, s), 7.86 (1H, d, J=8.0 Hz). $^{13}$C NMR (100 MHz, CD$_3$OD) δ 18.3, 28.6 (2C), 29.8, 68.6, 73.4, 80.5, 118.3, 126.4, 129.6, 129.8, 131.9, 136.2, 137.0, 145.1, 147.2, 167.1.

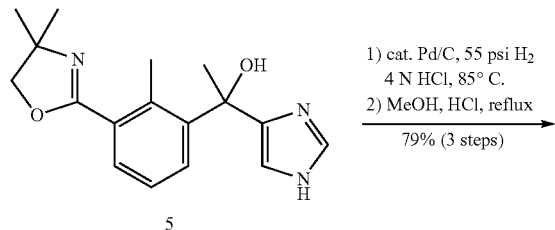

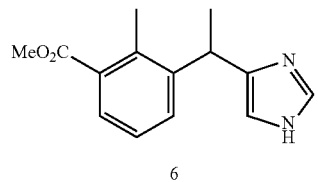

Procedure:

A 2 L heavy-walled pressure bottle was charged with 5 (crude, 162.8 g), 10 wt % Pd/C (25.0 g), a magnetic stir bar, and aqueous 4 N HCl solution (1.35 L, prepared from 500 mL of 12 N HCl and 1 L of tap water). It was sealed, purged sequentially with N$_2$, and H$_2$ to 55 psi, and stirred vigorously in an 85° C. oil bath for 21 h. At this point, $^1$H NMR assay indicated that the reaction was complete. The batch was filtered through a Celite pad (150 g, packed with 200 mL of HPLC grade water), and the filter cake rinsed with 50% MeOH-HPLC grade water (1 L). Filtrates were concentrated under reduced pressure, and the wet residue was co-evaporated with dry MeOH (500 mL×3). The batch was dissolved in MeOH (2.0 L), 4 M HCl in dioxane (1 L) was added, and the mixture was heated at 65° C. for 16 h. At this point, HPLC analysis indicated that the reaction was complete. Heating was halted and the batch concentrated under reduced pressure. The resulting thick syrup/solid was cooled in an ice-water bath and treated with saturated aqueous NaHCO$_3$ (1.8 L, prepared from 450 g of NaHCO$_3$ dissolved in 3.1 L of tap water). The pH of the mixture was found to be 8-9. Tap water (500 mL) was added to the mixture, which was extracted with EtOAc (2 L×4). The separated organic layers were combined and divided into 2 portions for ease of handling. Each was washed with brine (500 mL, prepared from 1.0 kg of NaCl dissolved in 2 L of tap water). The combined organic phases were dried over anhydrous MgSO$_4$ (200 g), filtered, and concentrated under reduced pressure to afford a wet solid. This material was swished in 50% EtOAc-hexane (2.0 L) for 16 h. The slurry was filtered and the filter cake rinsed with 10% EtOAc-hexane (500 mL). Drying under high vacuum for 16 h gave 94.8 g (79%) of 6 as a white powder. This filtrate was concentrated under reduced pressure and the residue was swished with 10% EtOAc-hexane (300 mL) for 3 h. Solids were collected on a filter and the filter cake was rinsed with 10% EtOAc-hexane (40 mL). Drying under high vacuum afforded an additional 9.4 g (8%) of 6 as a yellowish powder. LCMS (m/z) 245.16 (M$^+$+1). $^1$H NMR (400 MHz, CD$_3$OD) δ 1.55 (3H, d, J=6.8 Hz), 2.50 (3H, s), 3.87 (3H, s), 4.46 (1H, q, J=6.8 Hz), 6.74 (1H, t, J=1.2 Hz), 7.17 (1H, dd, J=8.0, 7.6 Hz), 7.26 (1H, dd, J=8.0, 1.2 Hz), 7.54 (1H, dd, J=7.6, 1.2 Hz), 7.57 (1H, d, J=1.2 Hz). $^{13}$C NMR (100 MHz, CD$_3$OD) δ 16.2, 21.3, 35.3, 52.6, 117.8, 126.8, 128.9, 131.4, 133.3, 136.4, 137.2, 143.0, 146.5, 171.1.

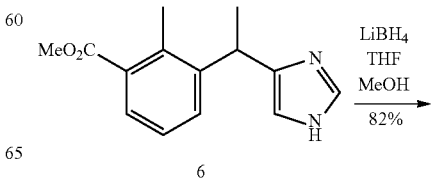

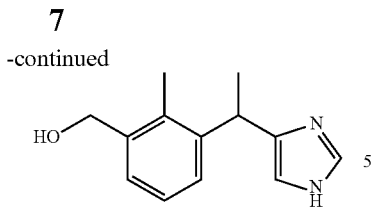

Procedure:

To a 250 mL single-necked flask equipped with a magnetic stirring bar and rubber septum containing a stirred suspension of 6 (1.0 g, 4.09 mmol) in THF (25 mL) under N$_2$ was added LiBH$_4$ (2.0 M in THF, 6.1 mL, 12.27 mmol) in one portion. To the resulting clear solution was added MeOH (1.0 mL then 2×0.5 mL) over 1 h. After 2 h, HPLC analysis indicated reaction had proceeded 22%. Additional LiBH$_4$ (2.0 M in THF, 6.1 mL, 12.27 mmol) and MeOH (2.0 mL) were added to the mixture in like fashion, and the batch was stirred for 16 h. At this time, analysis by HPLC indicated 96% conversion. Again, LiBH$_4$ (2.0 M in THF, 6.1 mL, 12.27 mmol) and MeOH (2.0 mL) were added and the mixture stirred for 2 h. This time, HPLC analysis indicated the reaction to be complete. Neat acetone (5.0 mL) was added drop wise to the mixture, resulting in an exothermic reaction in which the batch temperature rose to 38° C. The mixture was cooled with an ice-water bath. When cool, a 4 N aqueous HCl solution (5.5 mL, prepared from 100 mL of 12 N HCl and 200 mL of tap water) was added carefully to adjust the pH to 7. The batch was diluted with tap water (25 mL) and the resulting cloudy solution was extracted with EtOAc (3×100 mL). HPLC assay indicated that only the first two extracts contained product. All organic extracts were combined and dried over anhydrous MgSO$_4$ (16.2 g). The batch was filtered through a filter paper and the filter cake rinsed with EtOAc (100 mL). Filtrate and rinses were concentrated under reduced pressure. The residue was swished with EtOAc (50 mL) for 10 min while cooling with an ice-water bath, and then the solids were collected on a filter. The filter cake was rinsed with cold EtOAc (20 mL) and dried under high vacuum (1.18 g). The $^1$H NMR spectrum of this material suggested it to be an HCl salt; HPLC analysis showed one peak. The powder was suspended in tap water (30 mL) and 20 wt % aqueous NaOH solution (0.69 g); the pH of the mixture was 9. After vigorously stirring the mixture for 3 h, the batch was filtered and the filter cake was rinsed with MTBE (25 mL). Analysis by $^1$H NMR of this powder indicated it to be free base. The powder was dried in a vacuum over at 60° C. for 5 h to give 730 mg (82%) of compound according to Formula I as a white powder. mp=189-195° C. LCMS (m/z) 217.12 (M$^+$+1). $^1$H NMR (400 MHz, DMSO-d$_6$) δ 1.45 (3H, d, J=6.8 Hz), 2.24 (3H, s), 4.31 (1H, q, J=6.8 Hz), 4.49 (2H, d, J=3.6 Hz), 5.02 (1H, br s), 6.69 (1H, s), 7.00 (1H, br d, J=7.6 Hz), 7.06 (1H, t, J=7.6 Hz), 7.17 (1H, br d, J=7.6 Hz), 7.48 (1H, s), 11.75 (1H, br s). $^{13}$C NMR (100 MHz, DMSO-d$_6$) δ 13.4, 21.0, 33.3, 61.9, 116.5, 124.8, 125.1, 125.3, 132.6, 134.7, 140.1, 141.5, 144.0.

The synthesis may be summarized as follows:

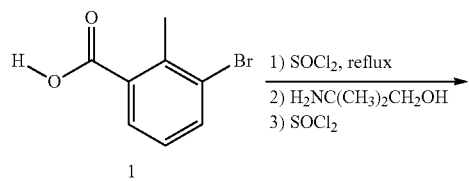

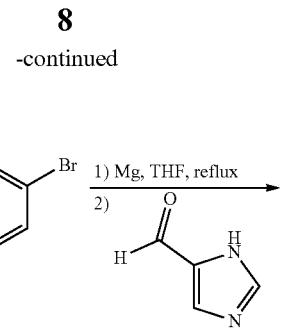

Methods of Use

The compounds of the invention may be used to treat chronic pain. To "treat," as used here, means to deal with medically. It includes administering a compound of the invention to prevent pain as well as to alleviate its severity.

Pain is of two types: chronic and acute. An "acute pain" is a pain of short duration having a sudden onset. One type of acute pain, for example, is cutaneous pain felt on injury to the skin or other superficial tissues, such as caused by a cut or a burn. Cutaneous nociceptors terminate just below the skin, and due to the high concentration of nerve endings, produce a well-defined, localized pain of short duration. "Chronic pain" is a pain other than an acute pain.

The compounds of the invention may be used to treat chronic pain. Chronic pain includes neuropathic pain, inflammatory pain, headache pain, somatic pain, visceral pain and referred pain.

I. Neuropathic Pain

The compounds of the invention may be used to treat neuropathic pain. Neuropathic pain includes pain associated with neuralgia, deafferentation, complex regional pain syndromes, and neuropathy.

1. Neuralgia

Neuralgia is a pain that radiates along the course of one or more specific nerves usually without any demonstrable pathological change in the nerve structure. The causes of neuralgia are varied. Chemical irritation, inflammation, trauma (including surgery), compression by nearby structures (for instance, tumors), and infections may all lead to neuralgia. In many cases, however, the cause is unknown or unidentifiable. Neuralgia is most common in elderly persons, but it may occur at any age. Neuralgia includes, for example, trigeminal neuralgia, spinal stenosis, postherpetic neuralgia, glossopharyngeal neuralgia, pain associated with nerve entrapment disorders, sciatica, and atypical facial pain.

2. Deafferentation

Deafferentation indicates a loss of the sensory input from a portion of the body, and can be caused by interruption of either peripheral sensory fibres or nerves from the central nervous system. Deafferentation pain syndrome includes, for example, post-stroke pain, phantom pain, and paraplegia.

3. Complex Regional Pain Syndromes (CRPSs)

CRPS is a chronic pain syndrome with two forms. CRPS 1 currently replaces the term "reflex sympathetic dystrophy syndrome." It is a chronic nerve disorder that occurs most often in the arms or legs after a minor or major injury. CRPS 1 is associated with severe pain; changes in the nails, bone, and skin; and an increased sensitivity to touch in the affected limb. CRPS 2 replaces the term causalgia, and results from an identified injury to the nerve.

4. Neuropathy

Neuropathy is a functional or pathological change in a nerve and is characterized clinically by sensory or motor neuron abnormalities. Central neuropathy is a functional or pathological change in the central nervous system.

Peripheral neuropathy is a functional or pathological change in one or more peripheral nerves. Either condition can lead to pain which may be treated by the compounds of the invention.

Some causes of neuropathy include heredity disorders, such as Charcot-Marie-Tooth disease, Friedreich's ataxia; systemic or metabolic conditions, such as diabetes, dietary deficiencies (especially vitamin B-12 deficiency), excessive alcohol use, uremia, and cancer; and infectious conditions, such as AIDS, hepatitis, and diphtheria; exposure to toxic compounds, such as the solvents used in industrial processes, heavy metals (lead, arsenic, mercury, etc.); and chemotherapy.

Neuropathy may involve a function or pathological change to a single nerve or nerve group (monneuropathy) or a function or pathological change affecting multiple nerves (polyneuropathy). Other types of neuropathy includes generalized peripheral neuropathies, distal axonopathies, myelinopathies, neuronopathies, and focal entrapment neuropathies, all of which can lead to chronic pain which may be treated by the compounds of the invention.

II. Inflammatory Pain

The compounds of the invention may be used to treat chronic pain associated with any of the following conditions: arthritis, such as rheumatoid arthritis, juvenile rheumatoid arthritis, systemic lupus erythematosus (SLE), gouty arthritis, scleroderma, osteoarthritis, psoriatic arthritis, and ankylosing spondylitis; connective tissue disorders, such as spondyloarthritis and dermatomyositis; injury, such as stretching of a tissue or joint, that results in chronic inflammatory pain; infection; neuritis, such as brachial neuritis and retrobulbar neuropathy; vestibular neuritis; and inflammation of the joints, such as that caused by bursitis or tendonitis.

III. Headache Pain

The compounds of the invention may be used to treat chronic pain associated with any of the following headache conditions. A headache (cephalgia) is a condition of mild to severe pain in the head. It may indicate an underlying local or systemic disease or be a disorder in itself. Examples of headaches include muscular/myogenic headache, such as tension headache; vascular headache, such as migraine, cluster headaches, and headaches resulting from high blood pressure; traction and inflammatory headaches resulting from other disorders such as stroke or sinus infection; hormone headache; rebound headache (medication overuse headaches); chronic sinusitis headache; organic headache; and ictal headaches.

IV. Somatic Pain

The compounds of the invention may be used to treat chronic pain associated with any of the following somatic pain conditions: excessive muscle tension, such as that caused by sprains or strains; repetitive motion disorders, such as those resulting from overuse of the hands, wrists, elbows, and shoulder; muscle disorders such as polymyositis, dermatomyositis, lupus, fibromyalgia, myalgia, polymyalgia rheumatica, macrophagic myofasciitis, and rhabdomyolysis; and muscle pain secondary to neurological and neuromuscular disorders;

V. Visceral Pain

The compounds of the invention may be used to treat chronic pain associated with any of the following visceral pain conditions. Visceral pain originates from body's viscera, or organs. Examples of visceral pain include the following: functional visceral pain, such as pain associated with functional irritable bowel syndrome, functional abdominal pain, functional constipation, functional dyspepsia, functional gastroesophageal reflux disease, and non-cardiac chest pain; pain associated with chronic gastrointestinal inflammation, such as gastritis, inflammatory bowel disease, Crohn's disease, ulcerative colitis, diverticulitis and gastroenteritis; pain associated with interstitial cystitis, urinary tract infections, pancreatitis and hernia.

VI. Allodynia

The A afferent fibers (A-beta and A-delta fibers) can be stimulated at a lower threshold than C fibers, and appear to be involved in the sensation of chronic pain. Under normal conditions, low threshold stimulation of these fibers (such as a light brush or tickling) is not painful. Under certain conditions such as those following nerve injury or in the herpes virus-mediated condition known as shingles the application of even such a light touch or the brush of clothing can be very painful. This condition is termed allodynia and appears to be mediated at least in part by A-beta afferent nerves. C fibers may also be involved in the sensation of chronic pain, but if so it appears clear that persistent firing of the neurons over time brings about some sort of change which now results in the sensation of chronic pain. The chronic pain associated with allodynia may be treated with the compounds of the invention.

Formulation and Administration

Compounds of the invention are formulated as pharmaceutical compositions. "Pharmaceutical composition," as used here, means a composition that is suitable for administering to human patients for the treatment of disease. In one embodiment, therefore, the compounds of the invention are formulated as pharmaceutically acceptable salts and further include one or more pharmaceutically acceptable excipients.

A "pharmaceutically acceptable salt" is any salt that retains the activity of the parent compound and does not impart any additional deleterious or untoward effects on the subject to which it is administered and in the context in which it is administered compared to the parent compound. A pharmaceutically acceptable salt also refers to any salt which may form in vivo as a result of administration of an acid, another salt, or a prodrug which is converted into an acid or salt. Pharmaceutically acceptable salts of acidic functional groups may be derived from organic or inorganic bases. The salt may comprise a mono or polyvalent ion. Of particular interest are the inorganic ions lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Hydrochloric acid or some other pharmaceutically acceptable acid may form a salt with a compound that includes a basic group, such as an amine or a pyridine ring.

Compounds of the invention may also be formulated as prodrugs. A "prodrug" is a compound which is converted to a therapeutically active compound after administration, and the term should be interpreted as broadly herein as is generally understood in the art. While not intending to limit the scope of the invention, conversion may occur by hydrolysis of an ester group or some other biologically labile group. Generally, but not necessarily, a prodrug is inactive or less active than the therapeutically active compound to which it is converted. Ester prodrugs of the compounds disclosed herein are specifically contemplated. While not intending to be limiting, an ester may be an alkyl ester, an aryl ester, or a heteroaryl ester. The term alkyl has the meaning generally understood by those skilled in the art and refers to linear, branched, or cyclic alkyl moieties. $C_{1-6}$ alkyl esters are particularly useful, where alkyl part of the ester has from 1 to 6 carbon atoms and includes, but is not limited to, methyl, ethyl, propyl, isopropyl, n-butyl, sec-butyl, iso-butyl, t-butyl, pentyl isomers, hexyl isomers, cyclopropyl, cyclobutyl, cyclopentyl, cyclohexyl, and combinations thereof having from 1-6 carbon atoms, etc.

Compounds of the invention may be administered orally, transdermally, topically, intraperitoneally, parenterally, subcutaneously, intranasally, intrathecally, intramuscularly, intravenously and intrarectally.

"Pharmaceutically acceptable excipients" refers to those ingredients comprising the vehicle in which the compounds of the invention are administered. Excipients are usually inert. Their selection depends on how the drug is to be administered. Compounds of the invention may be confected as a powder, pill, tablet or the like, or as a solution, emulsion, suspension, aerosol, syrup or elixir suitable for oral or parenteral administration or inhalation.

For solid dosage forms or medicaments, non-toxic solid carriers include, but are not limited to, pharmaceutical grades of mannitol, lactose, starch, magnesium stearate, sodium saccharin, the polyalkylene glycols, talcum, cellulose, glucose, sucrose and magnesium carbonate. The solid dosage forms may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in U.S. Pat. No. 4,256,108, No. 4,166,452, and No. 4,265,874, the contents of which are incorporated herein by reference, to form osmotic therapeutic tablets for control release.

Liquid pharmaceutically administrable dosage forms can, for example, comprise a solution or suspension of one or more of the presently useful compounds and optional pharmaceutical adjutants in a carrier, such as for example, water, saline, aqueous dextrose, glycerol, ethanol and the like, to thereby form a solution or suspension. If desired, the pharmaceutical composition to be administered may also contain minor amounts of nontoxic auxiliary substances such as wetting or emulsifying agents, pH buffering agents and the like. Typical examples of such auxiliary agents are sodium acetate, sorbitan monolaurate, triethanolamine, sodium acetate, triethanolamine oleate, etc. Actual methods of preparing such dosage forms are known, or will be apparent, to those skilled in this art; for example, see Remington's Pharmaceutical Sciences, Mack Publishing Company, Easton, Pa., 16th Edition, 1980. The composition of the formulation to be administered, in any event, contains a quantity of one or more of the presently useful compounds in an amount effective to provide the desired therapeutic effect.

The compounds of the invention may be administered at pharmaceutically effective doses. Such dosages are usually the minimum dose necessary to achieve the desired therapeutic effect; in the treatment of chronic pain, this amount would be roughly that necessary to reduce the discomfort caused by the pain to tolerable levels. For human adults such doses generally will be in the range of about 0.01-50 mg/kg/day, and often in the range of 0.05-25 mg/kg/day. However, the actual amount of the compound to be administered in any given case will be determined by a physician taking into account the relevant circumstances, such as the severity of the pain, the age and weight of the patient, the patient's general physical condition, the cause of the pain, and the route of administration.

The most effective pain-relieving drugs are also the most heavily sedating. The compounds of the invention, in contrast, can effectively relieve pain at doses that are non-sedating or only minimally sedating. "Sedating," as used here, means causing that level of sedation which would be described by a score of three or greater on the Stanford Sleepiness Scale. "Non-sedating" or "minimally sedating" means causing no more sedation than would be described by a score of 3 or less on the Stanford Sleepiness Scale. In this widely used measurement of alertness, a patient sits quietly with his eyes closed for one minute and then describes his current state of alertness using one of eight descriptions, as set forth below:

TABLE 1

Stanford Sleepiness Scale

| SCORE | DESCRIPTION |
| --- | --- |
| 1 | Feeling active, vital, alert, or wide awake |
| 2 | Functioning at high levels, but not at peak; able to concentrate |
| 3 | Awake, but relaxed; responsive but not fully alert |
| 4 | Somewhat foggy, let down |
| 5 | Foggy; losing interest in remaining awake; slowed down |
| 6 | Sleepy, woozy, fighting sleep; prefer to lie down |
| 7 | No longer fighting sleep, sleep onset soon; having dream-like thoughts |
| X | Asleep |

In one embodiment, Compound I (or one or both of its enantiomers) is administered to a patient to treat chronic pain at a dose that results in a sleepiness score of no more than 1 on the Stanford Sleepiness Scale. In another embodiment, Compound I (or one or both of its enantiomers) is administered to a patient to treat chronic pain at a dose that results in a sleepiness score of no more than 2 on the Stanford Sleepiness Scale. In another embodiment, Compound I (or one or both of its enantiomers) is administered to a patient to treat chronic pain at a dose that results in a sleepiness score of no more than 3 on the Stanford Sleepiness Scale.

At high doses the compounds of the invention are sedating. Hence, in another embodiment, Compound I (or one or both of its enantiomers) is administered to a patient to treat chronic pain at a dose that results in a sleepiness score of four or greater on the Stanford Sleepiness Scale.

The invention is further illustrated below using the following Examples.

EXAMPLES

Example 1

Analgesia Vs. Sedation

Compound I (racemic mixture) was assayed for its ability to alleviate sulprostone-induced tactile hypersensitivity and for sedating activity at various doses. The tactile hypersensitivity of 5-6 mice (weighing approx. 25 g) per group was scored every five minutes between 15 and 50 minutes following intraperitoneal dosing with 300 ng/kg (in a 1 mL/kg volume) sulprostone (Cayman Chemical Company, Ann Arbor, Mich.). Compound I or vehicle was administered intraperitoneally 15 minutes prior to sulprostone.

Tactile hypersensitivity was quantified by scoring the response of mice to light stroking of their flanks with a small paintbrush, which is not normally painful. The mice were rated on the following scale: a score of "2" was given to animals showing aggressive escape responses along with squeaking and biting at the brush; a score of "1" was given to animals exhibiting mild squeaking with attempts to escape; and a score of "0" was given if the animal showed no response to the light stroking of the paintbrush. The scores were summed to generate a cumulative score of 0 to 16 as described in Minami et al., *Pain* 57:217-223 (1994). Sulprostone-treated mice typically have a score of 14 and vehicle-treated mice typically have a score of 5-6. Chronic pain compounds including gabapentin and amitriptyline are active in this model consistent with effects in other chronic pain models and chronic pain patients, as described in Gil D W, Cheevers C V and Donello J E, *Br J Pharmacol* 153: 769-74 (2008).

In addition, the locomotor activity of 5-6 mice per group was measured in a five minute period 30 minutes following intraperitoneal dosing with compound I. The activity is determined automatically by placing the mice in an exploratory chamber (Omnitech Electronic) that has photocell beams criss-crossing the box that are interrupted as the animal moves around. The computer analyses this movement and records total activity. Locomotor activity relative to vehicle-treated animals was expressed as a percentage; percentage sedation was calculated as 100% minus the percent locomotor activity. Statistical calculations of significance for in vivo studies were done using a two-tailed Student's t-test.

As shown in Figures 1 and 2, Compound I administered at a dose of 1 mg/kg was minimally sedating and at a dose of 3 mg/kg was highly sedating. This was 10 fold-greater than the dose (0.3 mg/kg) that produced a reduction in sulprostone induced hypersensitivity back to control levels. Thus, compound I reduces pain at doses that are not sedating.

Example 2

Analgesia Vs. Sedation

Studies with Compound I and dexmedetomidine show that there is a >10-fold margin of safety for pain reduction vs. sedation with Compound I (Figure 3), but no margin for dexmedetomidine (Figure 4). They further show that Compound I is advantageous as an agent for relieving pain and can be taken systemically without the need for intravenous delivery.

Example 3

Activity in a FLIPR Assay

Compounds of the invention were evaluated in a FLIPR assay in order to determine their specificity for five alpha adrenergic receptors. The FLIPR assay measures release of intracellular calcium in response to receptor activation. Cells are preloaded with a calcium sensitive dye that fluoresces in response to calcium. Receptors that activate the G protein, Gq, elicit the response. Alpha adrenergic receptors, which normally couple to Gi, trigger the increase in intracellular calcium when coexpressed with a hybrid Gq protein containing a Gi receptor recognition domain, designated Gq/i5 (Conklin et al., *Nature* 363:274-6 (1993)) or with the promiscuous G protein $G_{\alpha 16}$.

The assay was performed essentially as follows. HEK 293 cells stably expressing an alpha-2 receptor and either the chimeric G-protein Gqi5 or the promiscuous G protein G16 were plated in poly-D-lysine coated 384-well plates at 20,000-25,000 cells per well and grown overnight in DMEM supplemented with 10% FBS. Cells were washed twice with HBSS/HEPES Buffer (1× Hanks Buffered Salt Solution, 20 mM HEPES, pH 7.4) prior to the addition of Fluo-4-AM (4 μM Fluo-4-AM, 0.04% pluronic acid in HBSS/HEPES Buffer), a calcium-sensitive dye. Cells were loaded with dye for 60 minutes at 37° C., then washed 4 times with HBSS/HEPES Buffer. The reaction was initiated by the addition of the appropriate dilutions of compounds (final concentration between 0.64 nM-10,000 nM) and the transient calcium signal captured. The peak height of the calcium curve was determined and utilized for calculation of $EC_{50}$ and efficacy using ActivityBase.

Table 2, below, shows agonist and antagonist activity at the alpha-1A, alpha-1B, alpha-2A, alpha-2B, and alpha-2C adrenergic receptors. Data in the first line in each column shows agonism; the first number is the $EC_{50}$, with the relative efficacy as compared to norepinephrine in parenthesis. Data in the second line, when present, shows antagonism; the first number is the $IC_{50}$, with the percent antagonism in parenthesis. As shown in Table 2, the (R) enantiomer of Compound I is an alpha-2C and alpha-2B agonist, and an alpha-2A antagonist. The (S) enantiomer is an alpha-2 pan agonist having some alpha-1A agonist activity. The racemate (Compound I) is an alpha-2 pan agonist having some alpha-1A agonist activity.

TABLE 2

| Activity in a FLIPR assay | | | | | |
|---|---|---|---|---|---|
| Compound | α-1A | α-1B | α-2A | α-2B | α-2C |
| Compound I | 1632 (.69) | >10000 >8300 | 53.7 (.75) | 5.5 (.94) | 15.7 (.98) |
| Compound II | >10000 nd (39%) | >10000 >8300 | >10000 144 (96%) | 52.8 (.68) | 171 (.64) |
| Compound III | 445 (.76) | >8300 | 72 (.9) | 3 (.93) | 8 (1) |

What is claimed is:

1. A pharmaceutical composition comprising an ester prodrug of a compound of the formula:

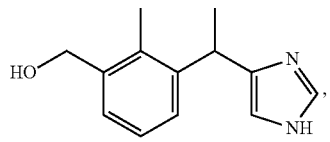 [SMILES: Cc1c(CO)cccc1C(C)c1c[nH]cn1 ; ","]

wherein the ester is an alkyl ester, an aryl ester or a heteroaryl ester.

2. The pharmaceutical composition of claim 1, wherein the composition comprises an ester prodrug of a compound of the formula:

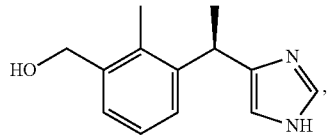 [SMILES: Cc1c(CO)cccc1[C@@H](C)c1c[nH]cn1 ; ","]

wherein the ester is an alkyl ester, an aryl ester or a heteroaryl ester.

3. The pharmaceutical composition of claim 1, wherein the composition comprises a compound represented by

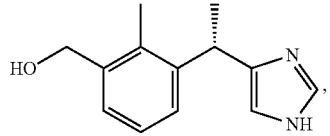 [SMILES: Cc1c(CO)cccc1[C@H](C)c1c[nH]cn1 ; ","]

wherein the ester is an alkyl ester, an aryl ester or a heteroaryl ester.

4. The pharmaceutical composition of claim 1, wherein the ester is an alkyl ester.

5. The pharmaceutical composition of claim 2, wherein the ester is an alkyl ester.

6. The pharmaceutical composition of claim 3, wherein the ester is an alkyl ester.

7. The pharmaceutical composition of claim 1, wherein the ester is a $C_{1-6}$ alkyl ester.

8. The pharmaceutical composition of claim 2, wherein the ester is a $C_{1-6}$ alkyl ester.

9. The pharmaceutical composition of claim 3, wherein the ester is a $C_{1-6}$ alkyl ester.

10. The pharmaceutical composition of claim 7, wherein the alkyl part of the ester is selected from the group consisting of methyl, ethyl, propyl, isopropyl, n-butyl, sec-butyl, isobutyl, t-butyl, pentyl isomers, hexyl isomers, cyclopropyl, cyclobutyl, cyclopentyl and cyclohexyl.

11. The pharmaceutical composition of claim 8, wherein the alkyl part of the ester is selected from the group consisting of methyl, ethyl, propyl, isopropyl, n-butyl, sec-butyl, isobutyl, t-butyl, pentyl isomers, hexyl isomers, cyclopropyl, cyclobutyl, cyclopentyl and cyclohexyl.

12. The pharmaceutical composition of claim 9, wherein the alkyl part of the ester is selected from the group consisting of methyl, ethyl, propyl, isopropyl, n-butyl, sec-butyl, isobutyl, t-butyl, pentyl isomers, hexyl isomers, cyclopropyl, cyclobutyl, cyclopentyl and cyclohexyl.

* * * * *